United States Patent [19]

Choporis et al.

[11] 4,036,224
[45] July 19, 1977

[54] PORTABLE CONDITIONED AIR BREATHING PIPE

[76] Inventors: Peter N. Choporis, 543 S. Beverly Lane, Arlington Heights, Ill. 60005; Robert N. Choporis, 880 N. Lake Shore Drive, Chicago, Ill. 60611

[21] Appl. No.: 621,372

[22] Filed: Oct. 10, 1975

[51] Int. Cl.² ............................................. A61M 15/06
[52] U.S. Cl. ...................................... 128/212; 128/208
[58] Field of Search ............... 128/208, 209, 210, 211, 128/212, 205, 206, 207, 192, 197, 198, 199, 200, 201, 195, 193, 185; 131/170 A, 171 A, 8 A

[56] References Cited

U.S. PATENT DOCUMENTS

| 801,555 | 10/1905 | Sprague | 128/192 |
|---|---|---|---|
| 1,262,846 | 4/1918 | Rider | 128/192 |
| 2,030,075 | 2/1936 | Robinson | 128/192 |
| 2,104,266 | 1/1938 | McCormick | 131/170 A |
| 2,450,610 | 10/1948 | Pierce | 128/208 |

FOREIGN PATENT DOCUMENTS

| 103,598 | 1/1926 | Austria | 128/201 |
|---|---|---|---|
| 451,230 | 4/1913 | France | 128/192 |
| 210,601 | 6/1907 | Germany | 128/212 |
| 808,270 | 7/1951 | Germany | 128/205 |
| 2,129,367 | 9/1972 | Germany | 128/210 |
| 343,589 | 2/1960 | Switzerland | 128/198 |

*Primary Examiner*—Robert W. Michell
*Assistant Examiner*—Henry J. Recla
*Attorney, Agent, or Firm*—Richard L. Johnston

[57] ABSTRACT

A portable conditioned air breathing pipe is provided in which a heat conductive tube having a burner or other suitable heating means therein is mounted in the pipe bowl in sealed relationship with a surrounding chamber which is connected through a tubular casing to a mouthpiece and fresh air is introduced into the surrounding chamber and heated so that heated air can be withdrawn through the mouthpiece to the mouth of the user. According to preferred embodiments, the outer surface of the heat conductive tube is provided with heat exchange fins, the interior of the heat exchange tube is provided with a heat economizer, the tubular casing is provided with a damper to admit cooler air and a filter is provided in the tubular casing between the heating chamber and the mouthpiece.

9 Claims, 5 Drawing Figures

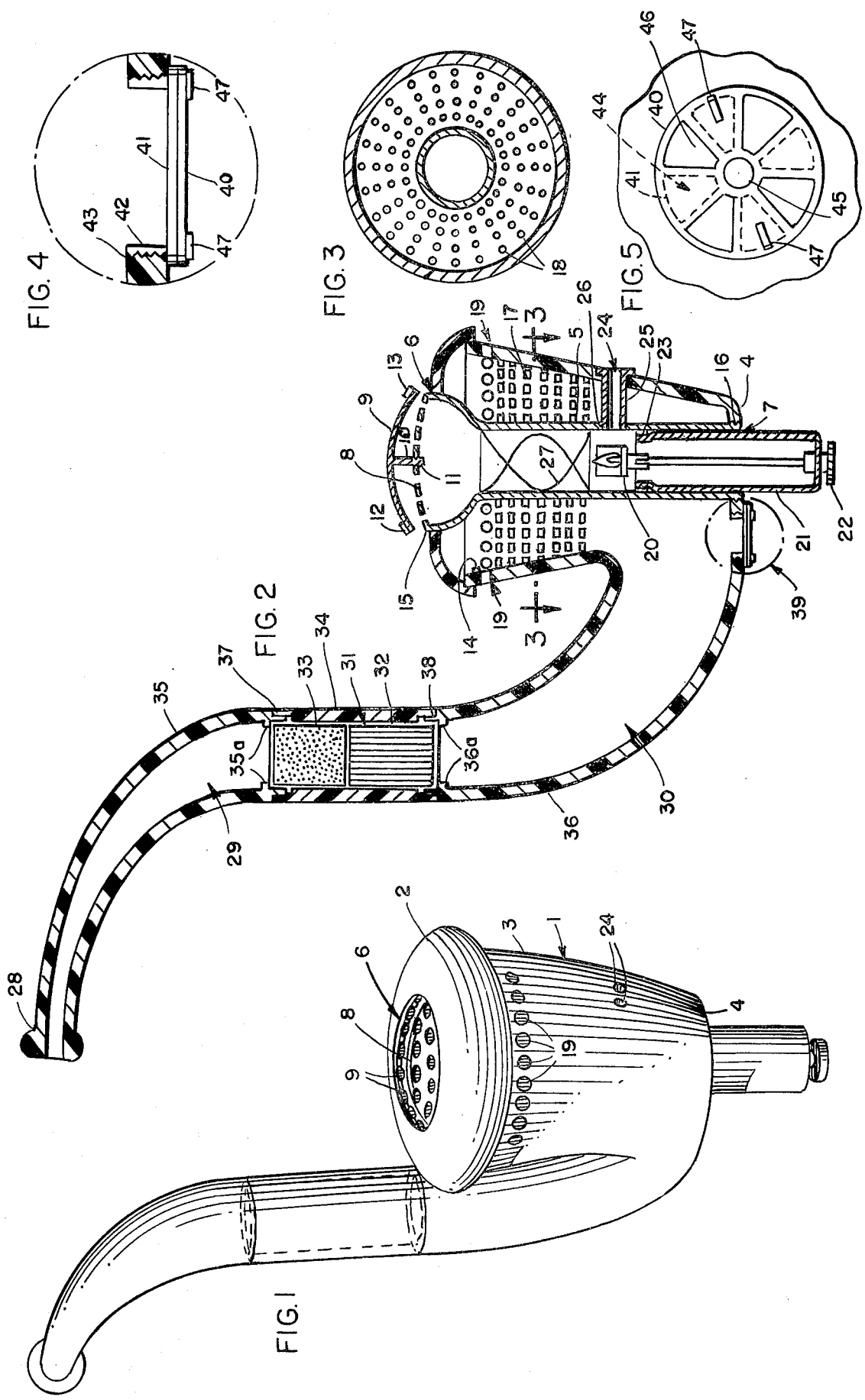

PORTABLE CONDITIONED AIR BREATHING PIPE

BACKGROUND

Various types of devices have been proposed for the purpose of introducing into the mouth of the user an inhalant or heated air. Thus, in U.S. Pat. No. 3,200,819 a device reassembling a cigarette is disclosed which contains an electrically heated bulb in order to warm the air. Other inhalant devices are disclosed in U.S. Pat. Nos. 933,360 and 3,320,953.

It would be desirable to have a portable conditioned air breathing pipe similar to a smoking pipe which could be used by persons suffering from cardio-respiratory ailments for the purpose of inhaling heated air without inhaling smoke or other inhalants when such persons are exposed to cold outside air. Devices which have been proposed for this purpose leave much to be desired.

OBJECTS

One of the objects of the present invention is to provide a new and improved type of portable conditioned air breathing pipe in which the air can be heated by using a smokeless, multi-jet type burner unit, burning a fuel such as butane and having the burning capacity and modulating range of the normal butane throw-away cigarette lighter.

Another object of the invention is to provide a device of the type described having a manually adjustable valve to permit modulating the flame size and thereby control the rate of degree of heating of the air passing through the device.

Still a further object of the invention is to provide a device of the type described in which the fuel supply consists of liquefied butane or similar gas fuel contained in a disposable or replaceable type container made of transparent nylon, metal or plastic.

Another object of the invention is to provide a device of the type described containing an air filter cartridge section which filters and purifies the heated air.

Still a further object of the invention is to provide a device of the type described containing an adjustable damper to permit mixing of cold air with heated air, thereby providing mixed air temperatures to suit the user's requirements.

Other objects and advantages of the invention will appear from the following description in conjunction with the accompanying drawings.

THE DRAWINGS

In the drawings:

FIG. 1 is a perspective view of a portable conditioned air breathing pipe provided in accordance with the invention;

FIG. 2 is a sectional view bisecting the pipe shown in FIG. 1;

FIG. 3 is a cross sectional view taken along the line 3,3 of FIG. 2;

FIG. 4 is a view, partly in section, of a portion of the pipe illustrated in FIG. 2; and FIG. 5 is a bottom plan view of the portion of the pipe shown in FIG. 4.

BRIEF SUMMARY OF THE INVENTION

In accordance with the invention, a portable conditioned air breathing pipe is provided in which a heat conductive tube having a burner or other suitable heating means therein is mounted in the pipe bowl in sealed relationship with a surrounding chamber which is connected through a tubular casing to a mouthpiece and fresh air is introduced into the surrounding chamber and heated so that heated air can be withdrawn through the mouthpiece to the mouth of the user. According to preferred embodiments, the outer surface of the heat conductive tube is provided with heat exchange fins, the interior of the heat exchange tube is provided with a heat economizer, the tubular casing is provided with a damper to admit cooler air and a filter is provided in the tubular casing between the heating chamber and the mouthpiece.

DETAILED DESCRIPTION OF THE INVENTION

As shown in FIGS. 1 and 2, the embodiment of the invention illustrated comprises a pipe bowl generally indicated at 1 having a top 2, sides 3, a bottom 4, a heat conductive tube 5 running from an opening 6 in the top 2 of bowl 1 to an opening 7 in the bottom of bowl 1. The tube 5 has a perforated metal cap 8 at the outer end thereof with openings or apertures 9 therein to permit the escape or emission of gasses.

The cap 8 is preferably protected by a weather cap 9 which is mounted on a stud 10 having threads 11 which intermesh with threads in the apertured cap 8 so that the weather cap can be removed. The weather cap 9 is arcuate and impervious to moisture so that rain or snow will run off around the edges without falling into the heat conductive tube 5. Bar strips 12 and 13 are provided which can be grasped by the fingers and used to rotate weather cap 9.

The space 14 between the outer surface of tube 5 and the inner surface of bowl 1 forms a heating chamber which is sealed with respect to tube 5 at 15 and 16 so that gases in tube 5 cannot enter the heating chamber 14. Tube 5 can be threaded at 16 as shown in FIG. 2 so as to engage intermeshing threads in the bottom 4 of bowl 1 at opening 7, thereby permitting the ready assembly and removal of tube 5. Tube 5 is preferably made of metal such as aluminum or any other heat conductive material, and the upper portion thereof is in contact with a heat exchanger 17 which consists of a number of fins or plates made of aluminum or other heat conducting material and having openings 18 therein as shown in FIG. 3 to permit the passage of air which is introduced through openings 19 to the heating chamber 14.

In the embodiment illustrated in the drawings, heat is supplied to the interior of tube 5 by a smokeless multi-jet burner unit 20 burning a fuel such as butane which is held in a storage unit 21. The burner unit has the burning capacity and modulating range of the normal butane throw-away type cigarette lighter and a manually adjustable valve 22 permits modulating the flame size and control of the rate and degree of heating of the air passing through the device. The container 21 is a disposable and replaceable type container made of transparent nylon or plastic or metal, or other suitable material, and is secured in tube 5 by means of intermeshed threads 23.

Outside air is admitted to the burner unit through openings 24 in one or more tubes 25 that are secured by means of threads or in any other suitable manner in the side of tube 5 at 26. The end of tube 25 at 26 is sealed with respect to the opening in tube 5 so that products of combustion or intake of air cannot pass into chamber 14.

A spiral metal heat economizer 27 is provided in tube 5 in order to increase the heating efficiency. The perforated metal fins which are expanded on the metal combustion tube 5 function as heat exchangers between the heated combustion tube and the air supply passing through the holes 18 in the perforated fins. Inasmuch as the heating chamber 14 is sealed from the combustion tube 5, the possibility of contamination of the air for breathing by the products of combustion inside the combustion tube is eliminated.

A mouthpiece 28 is connected to heating chamber 14 by passages 29 and 30. A removable air filter cartridge 31 is disposed between passages 29 and 30 in order to purify the air after it has been heated. If desired, this air filter cartridge section can also contain medication.

In the embodiment shown, the first section of the filter cartridge 32 located at the entering air section contains a high efficiency, non-allergic filter medium and the second section 33 contains activated carbon granules for a limited degree of air purification. The filter cartridge casing can be made of plastic or other suitable material with the top and bottom perforated to allow air to pass through the unit. The tubular section 34 which houses the filter cartridge 31 is connected to sections 35 and 36 of the casing which, enclose the passageways 29 and 30, by means of a press fit or by intermeshing threads at points 37 and 38. Projections 35a on the interior of section 35 and projections 36a on the interior of section 36 provide support for the filter cartridge 31.

In a preferred embodiment of the invention the device includes an adjustable damper which is shown encircled at 39 and is shown in more detail in FIGS. 4 and 5. As shown in FIGS. 4 and 5 the damper consists of a pair of apertured plates 40 and 41 made of metal or other suitable material which are mounted on a screw-type male fitting 42 having external threads which intermesh with threads in the casing 36 at 43 so that, if desired, the damper can be removed for cleaning purposes. The plate 41 is fixed to the fitting 42 and contains four apertures 44. The plate 40 is mounted for rotation around pivot point 45 and contains four blades 46 so that rotation of plate 40 opens and closes the apertures in plate 41. A pair of bar strips 47,47 is provided which can be grasped by the fingers in order to rotate plate 40. The adjustable damper permits mixing of cold air with heated air, thereby providing air having a temperature to suit the user's requirements.

OPERATION

In the operation of the device, the burner is ignited either by unscrewing it at 23 and withdrawing the burner unit and igniting it or by igniting it through passageway 24. Control valve 22 is turned to a position suitable to produce the desired flame necessary for the desired amount of heating. Fresh air enters through passageways 19 and combustion air enters through passageways 24. The products of combustion pass outwardly through perforated cap 8 and around the sides of weather cap 9, if a weather cap is being used.

As the hot products of combustion pass through tube 5 they heat the side walls which in turn supply heat to the heat exchanger 17 by conduction and radiation. The fresh air entering passageways 19 passes downwardly through the heat exchanger 17 in the heating chamber 14 into passageway 30 and then through filter 34 to passageway 29 and mouthpiece 28. The burner flame is adjusted manually through the valve system 22 to the exact requirements of the user thereby eliminating possible excess use of fuel and the consequent over heating of the device. The burner flame can be observed through the combustion air tube 24 and vessel inspection of the flame from time to time is a safety feature. Another safety feature is the air-tight compartment 14 whereby emission gases from the combustion are not intermingled with the intake air that is heated by the device and breathed by the user.

After the fresh air is heated by passing it through heat exchanger 17, it can be mixed with cold outside air through the damper indicated at 39 in order to provide air suited to the user's requirements.

When necessary or as prescribed by a physician, medication may be used by replacing the standard filter cartridge 31 with one containing medication saturated into the filter cartridge and passing fresh heated air through the medicated filter in order to provide heated medicated treatment for the user.

The invention is intended for portable use for outpatients susceptible to attacks of sundry cardio-respiratory ailments when such persons are exposed to cold outside air. Also, use by normal persons suffering from the "common cold" may find relief in the home or office or in transit with the use of this device. Older people, suffering from cariovascular or pulmonary disease may find comfort with the use of this device, especially when exposed to cold outdoor weather while walking or engaging in outdoor sports such as hunting, snowmobiling, or watching football. Normal persons using this device outdoors during severe cold weather will find comfort as well as endure the severe weather longer while participating in active winter sports such as skiing, tobagganing or skating.

It is thought that the invention and its numerous attendant advantages will be fully understood from the foregoing description, and it is obvious that numerous changes may be made in the form, construction and arrangement of the several parts without departing from the spirit or scope of the invention, or sacrificing any of its attendant advantages, the forms herein disclosed being preferred embodiments for the purpose of illustrating the invention.

The invention is hereby claimed as follows:

1. A portable conditioned air breathing pipe adapted to be supported by the mouth of the user comprising:
   a. a pipe bowl having a top, sides, and bottom, and a heat conductive tube running from an opening in the top of said bowl to an opening in the bottom of said bowl, a space surrounding the sides of said tube between the outer surface of said tube and the inner surface of said bowl, said tube having a first open end being sealed with respect to the opening in the top of said bowl and a second open end sealed with respect to the opening in the bottom of said bowl said space between the outer surface of said tube and the inner surface of said bowl forming a heating chamber,
   b. heating means mounted to heat said heat conductive tube of (a), said heating means comprising a burner unit having a container tubular fuel fitted into said opening in the bottom of said bowl and into the lower part of said heat conductive tube, and a jet burner on the top of said fuel container which when lit projects a flame upwardly into said tube,
   c. passageways between the outside of said bowl and said heating chamber to admit fresh air so that it contacts the heated surface of said heat conductive tube, d. a mouthpiece, and e. a rigid tubular casing connecting said mouthpiece and said heating chamber in the bowl of said pipe so that fresh air heated in said heating chamber can be withdrawn to the mouth of the user.

2. A portable conditioned air breathing pipe as claimed in claim 1 wherein said heating means comprises a jet burner unit burning a liquid fuel.

3. A portable conditioned air breathing pipe as claimed in claim 1 wherein said heating means comprises a burner unit which is removable.

4. A portable conditioned air breathing pipe as claimed in claim 1 wherein said pipe bowl contains a passageway from the outside of the pipe bowl to a point adjacent the combustion end of said burner unit.

5. A portable conditioned air breathing pipe as claimed in claim 1 wherein the opening to the atmosphere at the upper end of said heat conductive tube expand outwardly and contains an adjustable and removable weather cap.

6. A portable conditioned air breathing pipe as claimed in claim 1 wherein said tubular casing of (e) has a removable section which contains an air filter.

7. A portable conditioned air breathing pipe as claimed in claim 1 wherein said tubular casing of (e) contains an adjustable damper in a wall thereof for admission of outside air to be mixed with the heated air from said heating chamber.

8. A portable conditioned air breathing pipe as claimed in claim 1 in which said heat conductive tube is surrounded by a heat exchanger which conducts and radiates heat from said heat conductive tube to air passing through said heating chamber.

9. A portable conditioned air breathing pipe as claimed in claim 1 in which said heat conductive tube contains a spiral metal heat economizer.

* * * * *

UNITED STATES PATENT AND TRADEMARK OFFICE
CERTIFICATE OF CORRECTION

PATENT NO. : 4,036,224
DATED : July 19, 1977
INVENTOR(S) : PETER N. CHOPORIS and ROBERT N. CHOPORIS It is certified that error appears in the above-identified patent and that said Letters Patent are hereby corrected as shown below:

Column 4, line 61, "container tubular fuel" should read --tubular fuel container--.

Signed and Sealed this

Twenty-fifth Day of October 1977

[SEAL]

Attest:

RUTH C. MASON
*Attesting Officer*

LUTRELLE F. PARKER
*Acting Commissioner of Patents and Trademarks*